US007428455B2

(12) United States Patent
Corcoran

(10) Patent No.: US 7,428,455 B2

(45) Date of Patent: Sep. 23, 2008

(54) COMPACTION INDICATION BY EFFECTIVE ROLLING RADIUS

(75) Inventor: Paul T. Corcoran, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 732 days.

(21) Appl. No.: 10/963,027

(22) Filed: Oct. 12, 2004

(65) Prior Publication Data

US 2006/0080017 A1 Apr. 13, 2006

(51) Int. Cl.
*E01C 19/23* (2006.01)
*G01N 3/40* (2006.01)
*G06F 17/00* (2006.01)

(52) U.S. Cl. .............................. 701/50; 701/1; 701/35; 73/78; 404/125

(58) Field of Classification Search .................. 701/50, 701/35, 1; 73/78, 818; 404/125, 126; 250/34.8
See application file for complete search history.

(56) References Cited

U.S. PATENT DOCUMENTS 4,979,197 A 12/1990 Troxler, Sr. et al.
5,493,494 A 2/1996 Henderson
5,727,900 A * 3/1998 Sandstrom ................ 404/84.1
5,942,679 A * 8/1999 Sandstrom ..................... 73/78
5,952,561 A 9/1999 Jaselskis et al.
6,065,904 A * 5/2000 Cook et al. ................ 405/303
6,122,601 A 9/2000 Swanson et al.
6,188,942 B1 * 2/2001 Corcoran et al. ............. 701/50
6,460,006 B1 10/2002 Corcoran

* cited by examiner

*Primary Examiner*—Tan Q Nguyen
(74) *Attorney, Agent, or Firm*—Liell & McNeil

(57) ABSTRACT

Accurately determining the compaction state of a base material during the compaction process is a recognized problem in the construction industry. The present invention recognizes that the compaction state of the base material can be determined by ascertaining the effective roller radius of the compactor. In other words, in the case of powered compactors, the effective roller radius will asymptotically approach the actual roller radius as the base material changes from a soft uncompacted condition to a hard compacted state. Monitoring compaction state via indicative of an effective roller radius can be used alone as a means of determining compaction state in real time, or can be leveraged and combined with other independent means of monitoring the compaction state to a symbiotic affect in more accurately determining compaction state.

19 Claims, 2 Drawing Sheets

Smooth Roller
$R_E$
Tipped Roller
$R_E - R_S \geq H$ = Compacted "walk out"
Tip Radius $R_T$
Roller Radius $R_S$
Effective Radius
$R_S - R_E \leq X$ = Compacted
0
Soft
Compaction State
Powered Rollers
Hard Start
Read Sensor Input(s)
Determine Compaction State
Determine General Clearance
Determine Effective Roller Radius
Walkout ?
Link to Position Data
Record Data
Display Data
End

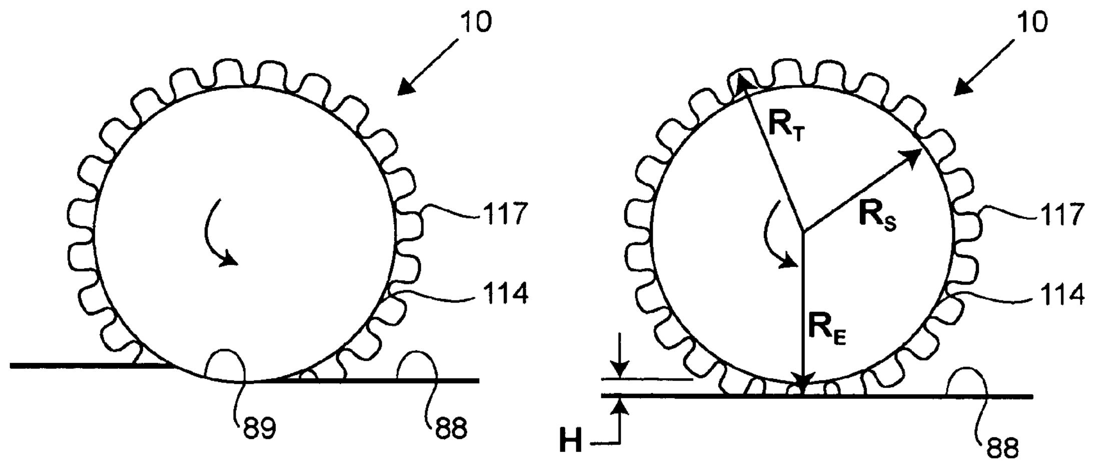
Figure 3a
Figure 3b
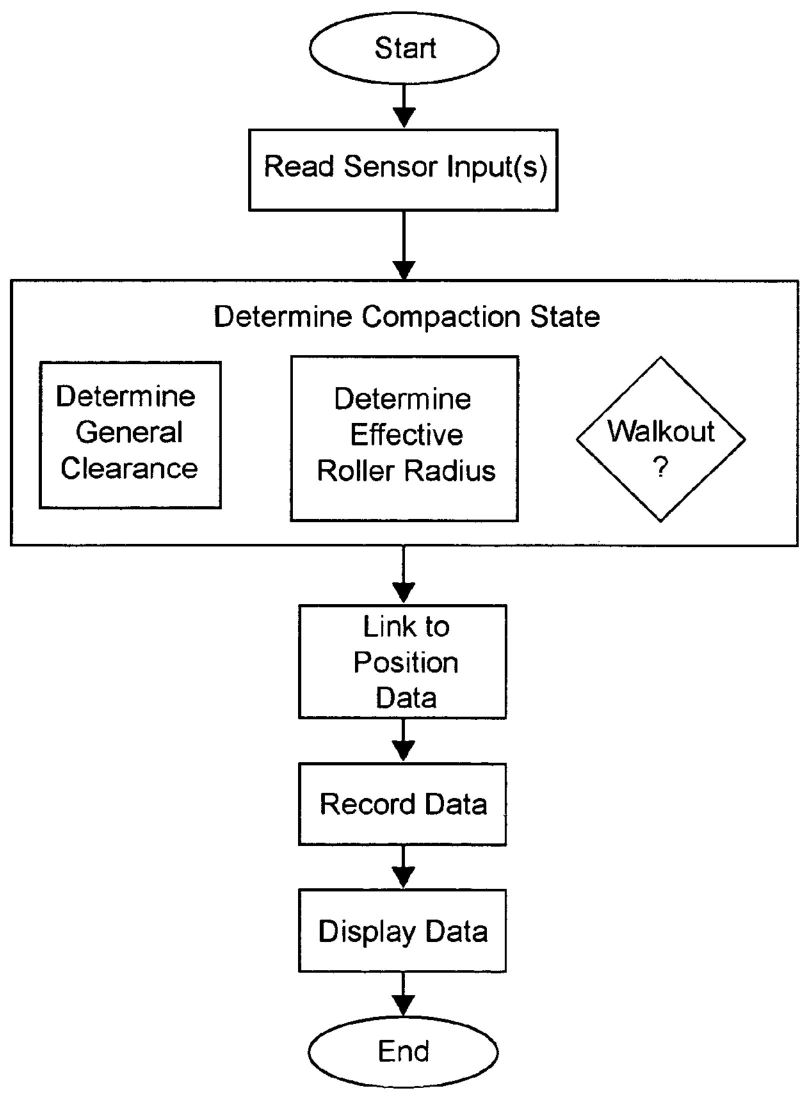
Figure 4

COMPACTION INDICATION BY EFFECTIVE ROLLING RADIUS

TECHNICAL FIELD

The present invention relates generally to compacting base materials with a compactor, and more particularly to a compaction state determination based upon data indicative of an effective roller radius of the compactor.

BACKGROUND

Proper compaction is a critical need to earthworks construction, road paving, landfills and the like. Current methods to measure compaction and insure the compaction meets job site requirements often depends on post process measurement methods such as nuclear density gages. These post process measurements often cause job delays and can fail to catch problems as they occur, thereby leading to rework or deviations from initial specifications. Thus, there is a need for reliably determining the compaction state of a base material while the compaction is occurring. In addition, there is a need to determine the compaction state accurately for the entire surface being compacted, as post process measurements normally test only a small fraction of the area being compacted.

Co-owned U.S. Pat. No. 6,188,942 to Corcoran et al. Responds to this need by teaching a method and apparatus for determining the performance of a compaction machine based on energy transfer. In one aspect, compaction state is determined by measuring the amount of energy required to propel the compactor over the base material. This reference recognizes that it takes more energy to propel a compactor over soft material than hard material. In another aspect, the compaction state of the base material is determined by measuring an amount of energy put into the base material by the compactor. Although the strategy taught in this reference appears promising, there remains room for improvements and alternatives.

U.S. Pat. No. 5,952,561 to Jaselskis et al. teaches a real time asphalt pavement quality sensor using a differential approach in which a pair of sensors located in front and behind the roller, respectively, measure reflected signals from the asphalt surface. The reference suggests that the difference between the reflected signals provides an indication of the compaction state of the asphalt pavement. The reference seeks to determine whether the pavement has achieved an optimal level of compaction by comparing sensor readings from successive passes over the base material. This reference suffers from potential drawbacks not only from inaccuracies in remotely measuring a feature of the asphalt material, but also suffers from potential problems relating to exposing sensors to hostile and often dirty work environments.

The present invention is directed to responding to the need for determining compaction state and/or improving upon the determination of compaction state.

SUMMARY OF THE INVENTION

In one aspect, a method of determining a compaction state of a base material includes a step of moving a compactor over the base material. Data is gathered that is indicative of an effective roller radius of the compactor. The compaction state data is determined for the base material using the data indicative of an effective roller radius.

In another aspect, a compactor includes a roller rotatably attached to a chassis. A compaction state determiner includes an electronic system carried by the chassis. The electronic system includes at least one sensor for producing sensor data related to an effective roller radius.

BRIEF DESCRIPTION OF THE DRAWINGS

FIG. 3*a* and FIG. 3*b* are side views of a tipped roller when the base material is soft and hard, respectively; and FIG. 4 is a flow diagram of a compaction algorithm according to the present invention.

DETAILED DESCRIPTION

Figure 1:
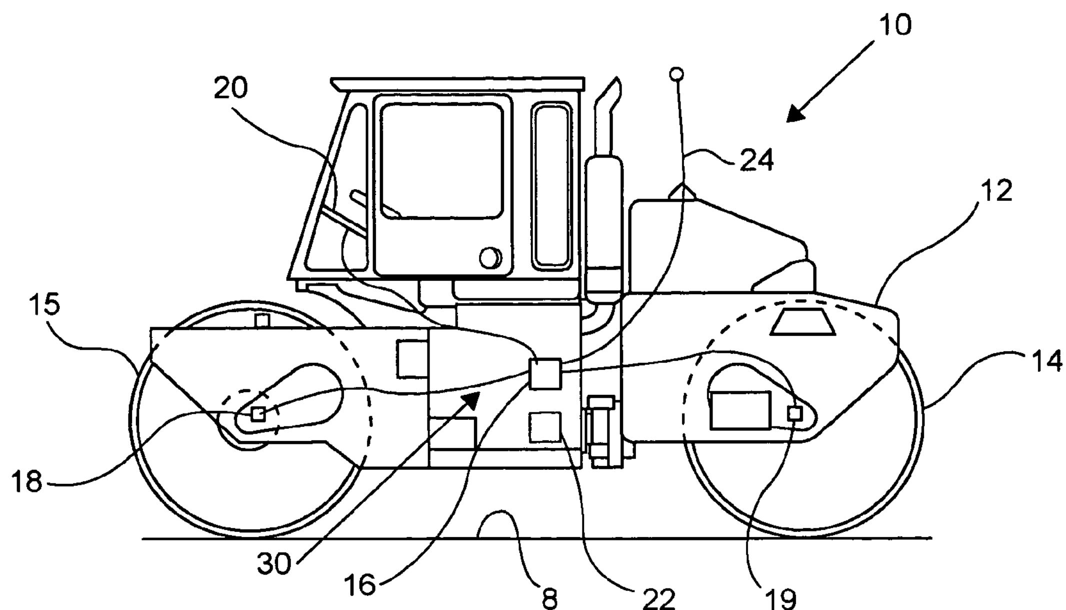
FIG. 1 is a side diagrammatic view of a compactor according to one aspect of the present invention.

Referring to FIG. 1, a compactor 10 includes a pair of rollers 14 and 15 that are rotatably attached to a chassis 12. Although compactor 10 is self propelled, the present invention finds potential application to towed compacting rollers as well. In addition, although rollers 14 and 15 are shown as smooth for an application such as asphalt, the present invention also finds potential application to tipped rollers used in applications such as compacting waste in a landfill or compacting soil for other earthworks construction. Compactor 10 includes an onboard computer 16 that can receive signals from various inputs including a sensor 18, sensor 19 and a position data receiver 24. Computer 16 includes a compaction algorithm that processes the sensor data to determine a compaction state of the base material 8, preferably in real time as compactor 10 is moving over the base material. This compaction data can then be stored in data storage device 22 and/or displayed to an operator on display panel 20.

Depending upon the particular compactor and the chosen strategy, sensors 18 and 19 can take on a variety of forms. For instance, in one aspect, sensors 18 and 19 can be roller rotation sensors, which could sense roller angular position and/or rotation rate of the respective rollers 15 and 14. In another aspect, sensors 18 and 19 could be ground clearance sensors that measure the ground clearance level of chassis 12 above the adjacent base material 8.

Figure 2:
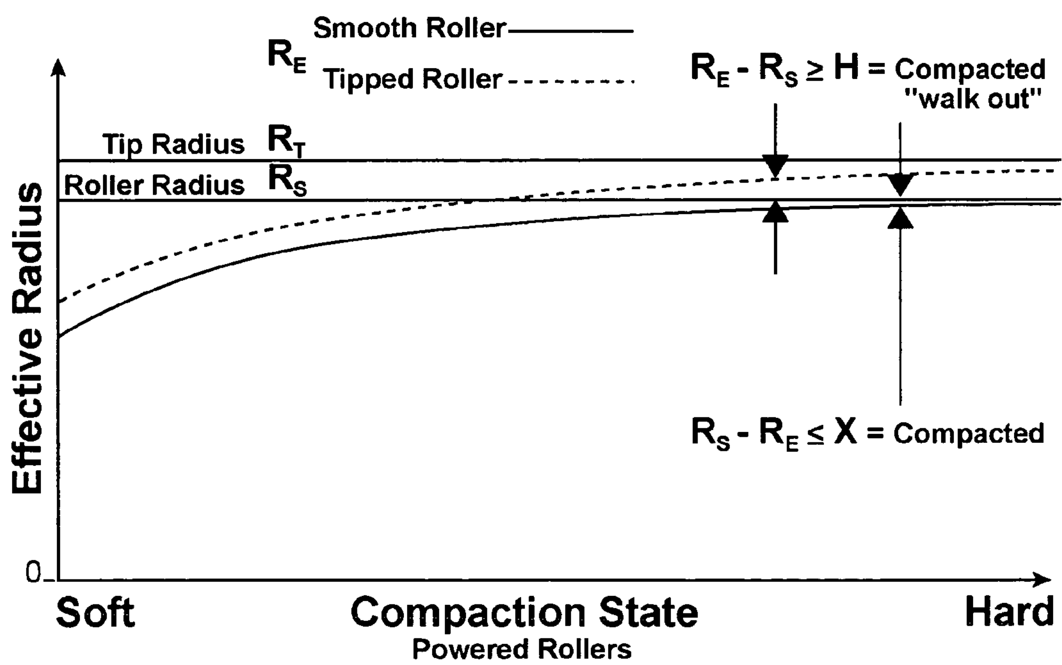
FIG. 2 is a graph of effective roller radius to compaction state for both tipped and smooth powered rollers according to the present invention.

Referring to FIG. 2, the present invention recognizes that the effective roller radius of a compactor will change as a base material is being compacted. Effective rolling radius $R_e$ is defined as the compactor travel distance per wheel revolution divided by two pi. When the compactor 10 of FIG. 1 begins a compacting job, it will start somewhere on the solid curved line. In other words, when the compacting job is initiated, the base material will be relatively soft and the effective radius of the roller will be substantially and measurably smaller than the actual roller radius $R_s$. As the material becomes harder with each pass of the compactor, one will move toward the right on the solid curved line. As the number of passes increases, the effective radius $R_e$ will asymptotically approach the actual radius $R_s$. When the difference X between the actual roller radius $R_s$ and the effective roller radius $R_e$ is less than some predetermined quantity, the base material can be said to be compacted. Those skilled in the art will recognize that the present invention insightfully recognizes that the compaction state of the underlying base material can be determined by measuring how well the base material supports the compactor. This in turn is determined by the effective rolling radius of the compactor as it moves over the base material.

One way of determining a target effective roller radius that would be useful by the operator in determining when the underlying material is sufficiently compacted would be to operate the compactor on a ground condition equal to the target level of compaction. The effective rolling radius on that already compacted ground could then be used as the target effective roller radius for compacting similar material under similar conditions. In addition, one might generate a database that correlates effective roller radius with compaction state for a variety of different base materials under a variety of different conditions, which may or may not include ambient conditions such as moisture level. Alternatively, a portion of a base material could be compacted to a desired level and then the effective roller radius of the compactor when traveling over that base material could be determined. That effective roller radius could be used as a target effective roller radius for a remaining portion of the base material to be compacted.

Referring now in addition to FIGS. 3*a* and 3*b*, the compactor 110 with a tipped roller 114 is shown moving over a base material 88 when soft and when hard, respectively. In particular, base material 88 could be construction soil, and as compactor 110 moves forward, both the smooth portion of roller 114 and tips 117 compact the base material 88 in the region 89. The compaction state of base material 88 in FIG. 3*a* would be somewhere in the soft region of the dashed line representing effective radius of a tipped roller. After a number of passes over a base material 88, compactor 110 would arrive at the state shown in FIG. 3 being where the smooth surface of roller 114 is actually lifted out of contact with base material 88 by the weight of the compactor being supported on tips 117. When the clearance distance between the smooth surface of the roller 114 and the base material 88 is greater than a distance H, the construction soil can be said to be compacted. Those skilled in the art will recognize that FIG. 3*b* is associated with a commonly observed phenomenon known as "walk out". "Walk out" is the response of the compaction machine as ground density increases. It is the decrease in roller sinkage and compactor tip penetration that occurs as ground strength increases in the compaction process. "Walk out" is commonly used in the field and is typically based solely on visual information by sight managers and inspectors. The present invention preferably quantifies the compaction state by quantifying the distance H achieved when the compactor is in a so called "walk out" state.

Although the present invention is preferably implemented by actually determining the effective roller radius of the compactor at various locations on the base materials. Those skilled in the art will appreciate that the present invention can be practiced by utilizing a variable related to, but not necessarily the same as, effective roller radius. For instance, one such alternative measure would be to utilize ground clearance sensors to periodically measure the distance between the sensor (chassis location) and the surface of the adjacent base material not compacted in the current pass. Although the present invention encompasses such an alternative, it is not preferred for a number of reasons. Among these reasons would be that measuring ground clearance could be problematic and could require costly transducers, which themselves could be subject to damage or could lack robustness for adverse conditions of dust and mud. In addition, the base material is rarely smooth and is most often irregular, thus requiring a topography or smoothing algorithm to determine what the average level of an irregular base material surface is. Nevertheless, those skilled in the art will appreciate that a wide variety of choices could be made with regard to ground clearance sensors including contact or non-contact devices. The ground clearance sensors could include but are not limited to sonic, infrared, radar and even gage wheels.

In a more preferred alternative, a likely more robust method would not require ground interacting transducers. In this alternative method, the relative wheel rolling radius can be determined from known compactor ground speed and a determined roller rotation speed. The availability of ground position through technology such as the global positioning system (GPS) makes the measure of true ground speed very accurate and available. Nevertheless, there are also alternatives to position information to measure true ground speed such as radar devices or even using a gage wheel. Wheel speed can easily be measured with any of the known transducers often used for rotational drive line or wheel hub speed sensing. Combining these two measures and comparing the difference between the two will reveal the compaction state of the base material. Recalling, effective rolling radius is defined as the machine travel distance per wheel revolution divided by two pi.

Referring to FIG. 4, an example compaction algorithm 50 is illustrated in the manner of a flow diagram. Those skilled in the art will appreciate that computer 16 of FIG. 1 would be programmed to include compaction algorithm 50. Compaction algorithm 50 initially includes a step of reading the sensor inputs 51. Next, the sensor input data is used by a compaction state determination algorithm 52 to determine the compaction state of the base material. In a preferred embodiment, this is done using an effective roller radius determiner 54 that utilizes the insight from the graph of FIG. 2 to determine the compaction state, preferably in real time, by a comparison of the actual roller radius to the effective roller radius. In the case of a tipped roller, such as that used for soil or waste compaction, the compaction state determination algorithm 52 might also include a walk out determiner 53, and/or a ground clearance determiner 55. For instance, if the sensor is used for a ground clearance determination, one could expect the compaction algorithm 50 to utilize the ground clearance determiner 55. However, in most instances the invention will use the effective roller radius determiner 54 as the primary portion of its compaction state determination algorithm 52. After the compaction state has been determined, the compaction state data is linked to position data so the compaction state of the entire surface can be mapped. Next, the data is recorded at step 58 and finally displayed in step 59. Those skilled in the art will appreciate that the display can take on a variety of forms, but is preferably graphical in nature, which may include colors or gray scales to indicate the level of compaction in each unit area of the base material. Thus, the operator could view their display and quickly determine where and how to operate the compactor to most efficiently compact the base material and to ascertain when the base material is completely compacted.

INDUSTRIAL APPLICABILITY

The present invention finds potential application in any compactor that includes a roller. Although the present invention has been illustrated in the context of powered smooth or tipped rollers, the present invention also finds potential application in the case of towed rollers. However, those skilled in the art will appreciate in the case of towed rollers, the effective radius of the roller will start out greater than its actual radius and will approach from above the actual radius as the base material is compacted. This is the opposite of the powered rollers illustrated in FIG. 2 that approach the actual radius from below. Nevertheless, those skilled in the art will appreciate that the same principals used with regard to powered rollers to determine compaction state based upon data indicative of effective roller radius could also apply to towed rollers as well. However, those skilled in the art will recognize that there would be a different calibration for a towed roller than for a powered roller.

When in operation, an operator activates electronic system 30 and initializes the compaction algorithm 50. As the compactor moves over the base material, sensors 18 and 19 gather data that is indicative of effective rolling radius. This data is processed according to the compaction algorithm in computer 16 to generate compaction state data for each location of the base material. This compaction state data can then be combined with position data to allow for generation of a compaction state map. Although the present invention illustrates the position data as being garnered from GPS information via a receiver 24, those skilled in the art will appreciate that the position data can be acquired in a number of other ways, known in the art which all fall into the intended scope of the present invention. In the case of tipped roller applications, the present invention might also include a walkout determiner and/or a ground clearance determiner that are themselves indicative of an effective roller radius. The present invention could be utilized alone or be combined with other compaction determination strategies to symbiotically improve real time evaluations of compaction state.

Those skilled in the art will appreciate that the effective roller radius of the compactor can be monitored in a number of ways. For instance, one could calculate a ratio of the actual ground speed to the rotation rate of the roller without ever actual calculating the effective roller radius. In addition, one could also monitor effective rolling radius by determining the ratio of ground distance traveled to the number of rotations undergone by the roller to traverse that distance. Thus, those skilled in the art will appreciate that the invention can be practiced by merely sensing data indicative of an effective roller radius rather than actually calculating effective roller radius in order to ascertain the compaction state of the base material.

The present invention advantageously provides a means for determining and displaying compaction state data in real time during a compacting operation. This information can be used by the operator to more efficiently maneuver the compactor over the base material to hasten the rate at which the entire surface is compacted. In addition, the present invention should allow for quality control compaction data over an entire surface that will allow for a reduction in a need for costly rework and adjustment to specifications due to a failure to meet compacting specifications at one or more locations on the base material. The present invention recognizes that there may be no better determination of compaction status than the ability of the base material to support the compactor with deflection less than some predetermined value. In the case of a smooth roller, this value X relates to a maximum acceptable difference between the actual radius and the effective radius of the compactor when the material is hard and suitably compacted. In another aspect for tipped rollers, walk out has occurred, and hence the ground is compacted, when the difference between the effective radius and the smooth surface of the roller is greater than or equal to some walk out height H.

It should be understood that the above description is intended for illustrative purposes only, and is not intended to limit the scope of the present invention in any way. Thus, those skilled in the art will appreciate that other aspects, objects, and advantages of the invention can be obtained from a study of the drawings, the disclosure and the appended claims.

What is claimed is:

1. A method of determining a compaction state of a base material, comprising the steps of:

moving a compactor over the base material;

gathering data indicative of an effective roller radius of the compactor; and determining compaction state data for the base material using the data indicative of an effective roller radius.

2. The method of claim 1 wherein the determining step includes a step of determining whether the compactor is in a walk out state with respect to the base material at least in part using the compaction state data.

3. The method of claim 1 wherein the gathering step includes a step of determining ground clearance data indicative of a distance between a location on the compactor and the base material.

4. The method of claim 1 including a step of linking compactor position data to the compaction state data.

5. The method of claim 1 including displaying the compaction state data to a compactor operator during the moving step.

6. The method of claim 1 including a step of recording the compaction state data.

7. The method of claim 1 including a step of determining a target effective roller radius at least in part by moving the compactor over a material that already has a desired compaction state.

8. A method of determining a compaction state of a base material, comprising the steps of:

moving a compactor over the base material;

gathering data indicative of an effective roller radius of the compactor;

determining compaction state data for the base material using the data indicative of an effective roller radius; and the gathering step includes the steps of:

determining ground speed data indicative of a ground speed of the compactor; and determining rotation speed data indicative of a rotation speed of a roller of the compactor.

9. The method of claim 8 including a step of determining a ratio using the ground speed data and said rotation speed data.

10. A method of determining a compaction state of a base material, comprising the steps of:

moving a compactor over the base material;

gathering data indicative of an effective roller radius of the compactor; and determining compaction state data for the base material using the data indicative of an effective roller radius;

the gathering step includes the steps of:

determining distance data indicative of a compactor travel distance for a time period; and determining revolution data indicative of a number of roller revolutions for the travel period.

11. The method of claim 10 including a step of determining a ratio using the distance data and the revolution data.

12. A compactor comprising:

a chassis;

a roller rotatably attached to said chassis;

a compaction state determiner that includes an electronic system carried by said chassis; and said electronic system including at least one sensor for producing sensor data related to an effective roller radius, and means, including an effective roller radius determination algorithm, for determining an effective roller radius of the roller.

13. The compactor of claim 12 wherein said at least one sensor includes a roller rotation sensor.

14. The compactor of claim 12 wherein said at least one sensor includes a ground clearance sensor.

15. The compactor of claim 12 including a compaction state display carried by said chassis.

16. The compactor of claim 12 wherein said electronic system includes an electronic data processor with a compaction state determination algorithm.

17. The compactor of claim 16 wherein said compaction state determination algorithm includes a walkout determination algorithm.

18. The compactor of claim 12 wherein the electronic system includes a data recorder.

19. The compactor of claim 12 wherein said electronic system includes a data processor, a roller rotation sensor and a position determiner.

* * * * *